(12) United States Patent
Koenigsmann et al.

(10) Patent No.: US 8,487,150 B2
(45) Date of Patent: Jul. 16, 2013

(54) PROCESS FOR HYDROGENATING BUTADIYNE

(75) Inventors: Lucia Koenigsmann, Stuttgart (DE);
Ekkehard Schwab, Neustadt (DE);
Piotr Makarczyk, Ludwigshafen (DE);
Kai Rainer Ehrhardt, Speyer (DE);
Maximilian Vicari, Limburgerhof (DE);
Thomas Heidemann, Viernheim (DE);
Dirk Grossschmidt, Mannheim (DE);
Gerrit Waters, Karlsruhe (DE)

(73) Assignee: BASF SE, Ludwigshafen (DE)

( * ) Notice: Subject to any disclaimer, the term of this patent is extended or adjusted under 35 U.S.C. 154(b) by 590 days.

(21) Appl. No.: 12/485,398

(22) Filed: Jun. 16, 2009

(65) Prior Publication Data

US 2010/0016646 A1    Jan. 21, 2010

(30) Foreign Application Priority Data

Jul. 18, 2008  (EP) ..................................... 08160686

(51) Int. Cl.
*C07C 7/167* (2006.01)

(52) U.S. Cl.
USPC ........... 585/259; 585/258; 585/275; 585/277; 585/250; 208/142; 208/143; 208/145

(58) Field of Classification Search
USPC .................. 585/250–279; 208/142, 143, 145
See application file for complete search history.

(56) References Cited

U.S. PATENT DOCUMENTS

| 3,086,022 | A | * | 4/1963 | Meltzer et al. | 546/188 |
| 3,325,972 | A | * | 6/1967 | Friz et al. | 585/539 |
| 4,128,595 | A | * | 12/1978 | Montgomery | 585/261 |
| 4,191,845 | A | * | 3/1980 | Rubin et al. | 585/253 |
| 6,388,150 | B1 | * | 5/2002 | Overbeek et al. | 585/260 |

FOREIGN PATENT DOCUMENTS

| DE | 875 198 | 4/1953 |
| DE | 1 051 845 | 3/1959 |
| DE | 1 057 094 | 5/1959 |
| DE | 1 468 206 | 5/1969 |
| DE | 44 22 815 A1 | 1/1996 |
| EP | 0 945 415 A1 | 9/1999 |

OTHER PUBLICATIONS

U.S. Appl. No. 13/128,895, filed May 12, 2011, Heidemann, et al.

\* cited by examiner

*Primary Examiner* — In Suk Bullock
*Assistant Examiner* — Sharon Pregler
(74) *Attorney, Agent, or Firm* — Oblon, Spivak, McClelland, Maier & Neustadt, L.L.P.

(57) ABSTRACT

In the process for hydrogenating butadiyne over a catalyst which comprises at least one platinum group metal on an inorganic metal oxide as a support, the hydrogenation is performed at a pressure in the range from 1 to 40 bar and a temperature in the range from 0 to 100° C., and from 0.05 to 5% by weight, based on the overall catalyst, of platinum group metal is present on the support.

8 Claims, No Drawings

PROCESS FOR HYDROGENATING BUTADIYNE

The invention relates to a process for hydrogenating butadiyne, wherein the butadiyne originates preferably from gas scrubbing in acetylene preparation, and to the use of a catalyst for hydrogenating butadiyne.

Acetylene is prepared by partial oxidation of hydrocarbons such as natural gas. Corresponding processes for preparing acetylene are described, for example, in DE-A-1 057 094 and DE-A-44 22 815. The resulting acetylene is generally purified by selective adsorption and desorption in a solvent such as N-methylpyrrolidone (NMP). At the same time, higher acetylenes such as butadiyne can polymerize and form inflammable and explosive compounds which tend to form gels, thus giving rise to a purification requirement.

The purification of acetylene is described, for example, in DE-A-1 468 206. In this method, monovinylacetylene and diacetylene are hydrogenated in an NMP solvent over a catalyst comprising palladium on aluminum oxide. It is stated that the hydrogenated products are nonpolymerizable and can be removed from the solvent simply by drawing them off. It is stated that the process can be performed at a pressure of from atmospheric pressure up to about 7 at gauge, preference being given to a pressure in the range from 1.75 at gauge to 3.5 at gauge. The temperature specified is from 25 to 200° C., preferably from 25 to 100° C. The process is not employable advantageously in the same way for all acetylene impurities.

EP-A-0 945 415 describes the removal of polyunsaturated compounds from $C_4$ cuts. It is stated that butadiene and alkynes or alkenynes can be hydrogenated selectively in a two-stage process. Compounds such as vinylacetylene can be removed from butadiene by extractive distillation.

It is an object of the present invention to provide a process for hydrogenating butadiyne, which hydrogenates butadiyne to butanes in high yields. The hydrogenation should be performable in a time-efficient manner and with a low level of complexity.

The object is achieved in accordance with the invention by a process for hydrogenating butadiyne over a catalyst which comprises at least one platinum group metal on an inorganic metal oxide as a support, wherein the hydrogenation is performed at a pressure in the range from 1 to 40 bar, preferably from 10 to 40 bar, and a temperature in the range from 0 to 100° C., preferably from 15 to 100° C., and from 0.05 to 5% by weight, based on the overall catalyst, of platinum group metal is present on the support.

It has been found in accordance with the invention that the hydrogenation of butadiyne can be performed particularly advantageously over a catalyst comprising a platinum group metal on an inorganic metal oxide as a support, when a pressure in the range from 10 to 40 bar and a temperature in the range from 15 to 100° C. are employed.

The invention additionally relates to the use of a catalyst which comprises at least one platinum group metal on an inorganic metal oxide as a support, wherein, based on the overall catalyst, from 0.05 to 5% by weight of platinum group metal is present on the support, for hydrogenating butadiyne.

The process according to the invention is performed at a pressure in the range from 1 to 40 bar, preferably from 10 to 40 bar, preferably from 10 to 30 bar, in particular from 10 to 20 bar. The temperature is from 1 to 100° C., preferably from 15 to 100° C., preferably from 20 to 90° C., in particular from 25 to 80° C., especially from 30 to 50° C.

The catalyst used comprises at least one platinum group metal on an inorganic metal oxide as a support, where the content of platinum group metal is from 0.05 to 5% by weight, preferably from 0.1 to 2.5% by weight, in particular from 0.2 to 1% by weight, in particular from 0.2 to 0.4% by weight. The platinum group metal used is more preferably palladium. Up to 20% by weight, preferably up to 10% by weight, of the palladium may be replaced by other platinum group metals. The catalyst more preferably comprises only palladium as the active metal. The support may be selected from any desired suitable inorganic metal oxides. Preference is given to using, as the catalyst support, aluminum oxide, titanium dioxide, zirconium oxide, silicon dioxide or a mixture of two or more thereof. More preferably, the support comprises aluminum oxide, and is especially an $Al_2O_3$ support, for example a γ-aluminum oxide support.

The catalyst support has a porosity of preferably from 0.2 to 1.0 ml/g, more preferably from 0.3 to 0.6 ml/g. The median pore volume is preferably in the range from 5 to 20 nm, preferably from 7.5 to 12.5 mm.

In the hydrogenation, the butadiyne is preferably present in an organic solvent other than hydrocarbons. The solvents used may preferably be N-methylpyrrolidone (NMP), dimethylformamide (DMF), acetone, furfurol, acetonitrile, dimethylacetamide or a mixture thereof. Particular preference is given to using N-methylpyrrolidone as the solvent.

The process can be performed in any desired suitable manner. Preference is given to performing the process in a fixed bed, for example in trickle mode, in which case the butadiyne or the solution comprising butadiyne is conducted through the catalyst bed. The catalyst is preferably present in fixed bed form, and the reaction is carried out in gas/liquid phase in a fixed bed (trickle mode).

Preference is given to performing the hydrogenation with a liquid circulation system, in which case a portion of the liquid is circulated. The hydrogenation of butadiyne to butane is a strongly exothermic reaction, and so it is advantageous to control and to remove the heat of reaction by means of a liquid circulation system with recycling. In the liquid circulation system, preference is given to working with a weight ratio of recycle stream to feed stream in the range from 2 to 20, more preferably from 3 to 10.

The pressure established in the reaction is preferably generated by hydrogen. Preference is given to establishing a molar ratio of hydrogen to butadiyne of from 10 to 100, especially from 10 to 50, and a liquid hourly space velocity (LHSV) of up to 15 $m^3$ of fresh feed per $m^3$ of catalyst per hour.

The butadiyne may originate from any desired suitable sources. The butadiyne preferably originates from gas scrubbing in acetylene preparation, for example from the bottom stream from an acetylene prescrubber. The acetylene is preferably prepared by partial oxidation of hydrocarbons, especially natural gas. In the partial oxidation, the oxidation products are preferably cooled by quenching, for example with oil or water. Corresponding processes are described in DE-A-1 057 094, DE-B-875 198, DE-A-44 22 815 and DE-A-1 051 845. The acetylene is preferably purified by selective absorption and desorption with NMP. This affords butadiyne in NMP as an extract. Preferably in accordance with the invention, this extract is used in the hydrogenation. The content of butadiyne in the solution is preferably from 1 to 10% by weight, more preferably from 2 to 5% by weight.

The composition used in the hydrogenation comprises frequently from 50 to 80% by weight of NMP, more preferably from 60 to 75% by weight of NMP. In addition, benzene and toluene may be present in significant amounts, for example in a total amount of from 10 to 40% by weight, preferably from 15 to 30% by weight.

In addition, frequently from 0.25 to 1.5% by weight of styrene is present.

An illustrative composition comprises from 1.5 to 2.5% by volume of butadiyne and from 0.5 to 1.5% by volume of styrene in NMP as the solvent. Such a mixture may be obtained, for example, from an acetylene stripper.

Typically, a stream which is obtained from the gas scrubbing of acetylene and has an organic solvent other than hydrocarbons is used, in which, based on butadiyne, up to 20% by weight of vinyl acetylene and up to 10% by weight of acetylene may be present. More preferably, up to 10% by weight of vinyl acetylene and up to 5% by weight of acetylene are present. Especially preferably, the proportion of acetylene is as low as possible, for example 5% by weight or less, and the proportion of vinyl acetylene is as low as possible, for example 5% by weight or less.

In the process according to the invention, there may be deactivation of the catalyst over prolonged periods, for example when greater amounts of styrene are present in the starting mixture. The catalyst can be regenerated by known processes. For example, the catalyst can be purged with nitrogen and then heated under nitrogen to temperatures in the range from 100 to 300° C., more preferably from 150 to 250° C. Subsequently, nitrogen can be replaced by superheated steam, and it can be heated further to temperatures of from 300 to 400° C. On attainment of this temperature, a portion of the steam can be replaced by air, for example from 1 to 10% by volume. Thereafter, the catalyst bed can be cooled, in the course of which steam is again replaced by nitrogen. Before a further use of the catalyst, it should be reduced once again. The regeneration of the catalyst is preferably performed at a pressure in the range from 1 to 5 bar, especially from 2 to 4 bar.

The butadiyne used in the process is preferably hydrogenated to butane and butenes. Particular preference is given to a minimum proportion of unsaturated compounds.

The invention is illustrated in detail by the examples which follow.

EXAMPLE 1

The catalyst used in the process comprised between 0.19 and 0.24% by weight of palladium on γ-aluminum oxide. The catalyst support was present in the form of spheres with a diameter in the range from 2 to 4 mm. The porosity was 0.4 to 0.5 ml/g, and the median pore volume was in the range from 8 to 11.5 nm.

Amounts of from 6.3 to 25 g of the catalyst were initially charged in a tubular reactor with an internal diameter of 4 mm. The total length of the catalyst bed was 360 cm. Four thermocouples were distributed over the length of the catalyst bed. Fresh starting mixture, recyclate and hydrogen were introduced into the reactor at the bottom. The exit stream from the reactor was divided in a separator into a gas stream and a liquid stream. The liquid stream was again divided into a recycle stream and a product stream. The recycle stream was fed to the reactor via a pump. The catalyst was reduced in the reactor before the start of the reaction under 10 l/h of hydrogen at 120° C. for 16 hours. The mixture used comprised from 1.5 to 3.5% by volume of butadiyne and from 0.5 to 1.5% by volume of styrene in NMP and was obtained from an acetylene stripper. The reaction temperature was in the range from 25 to 80° C. at a total pressure of from 10 to 20 bar (hydrogen from 1 to 1.5 l (STP)/h). The feed was 10 g/h of NMP solution. The recycle ratio was 1:4, i.e. 40 g/h of recycled mixture were conducted into the reactor with 10 g/h of fresh feed.

The liquid samples of the product were analyzed by gas chromatography. The column used was 150 m pertocol FD 1 μm, ID 0.25 mm, 35° C./20 min, 2° C./min to 140° C., 4° C./min to 250° C./40 min.

The mixture used in the process comprised, for example, from 61 to 74% NMP, from 0.3 to 0.5% styrene, from 8 to 12% toluene, ethylbenzene and xylene, from 8 to 22% benzene and from 3 to 4% butadiyne (area percent determined by gas chromatography).

Butadiyne was no longer detectable in the reaction product, as it had been hydrogenated to butane and butenes.

Overall experiments were carried out at 20° C. and 10 bar, 80° C. and 10 bar, and 40° C. and 20 bar. In each case, full butadiyne hydrogenation was achieved.

EXAMPLE 2

The process of example 1 was repeated, except that the reactor length was reduced to 90 cm. The amount of catalyst was 6.3 g, and 1.6 ml of fresh feed/g of catalyst per hour were employed. The reaction was effected at 40° C. and a pressure of 20 bar. Again, butadiyne was hydrogenated fully.

It becomes clear from the experiments that the hydrogenation of butadiyne in NMP as the solvent proceeds stably over a prolonged period at 20° C. and also at 40° C.

The invention claimed is:

1. A process for hydrogenating butadiyne to butane over a catalyst which comprises at least one platinum group metal on an inorganic metal oxide as a support, said process comprising:
   fully hydrogenating butadiyne, via a one-stage process, over the catalyst, at a pressure of from 1 to 40 bar, at a temperature of from 0 to 100° C., and with a liquid circulation system with a weight ratio of recycle stream to feed stream of from 2 to 20,
   wherein
   from 0.05 to 5% by weight, based on the total weight of the catalyst, of the platinum group metal is present on the support,
   the support has a porosity of from 0.2 to 1.0 ml/g,
   the hydrogenation is performed on a stream obtained from gas scrubbing of acetylene,
   the stream comprises an organic solvent other than hydrocarbons,
   the stream comprises up to 20% by weight of vinylacetylene and up to 10% by weight of acetylene, based on the weight of butadiyne, and
   the stream comprises from 1 to 10% by weight of butadiyne, based on the total weight of the stream.

2. The process according to claim 1, wherein the platinum group metal is palladium and the inorganic metal oxide is one or more selected from the group consisting of aluminum oxide, titanium dioxide, zirconium oxide, and silicon dioxide.

3. The process according to claim 1, wherein the butadiyne is present in an organic solvent other than hydrocarbons.

4. The process according to claim 3, wherein the organic solvent is one or more selected from the group consisting of N-methylpyrrolidone, dimethylformamide, acetone, furfurol, acetonitrile, and dimethylacetamide.

5. The process according to claim 1, wherein the hydrogenation of butadiyne is performed in a fixed bed.

6. The process according to claim 1, wherein the support has a porosity of from 0.3 to 0.6 ml/g.

7. The process according to claim 1, wherein the weight ratio of recycle stream to feed stream is from 3 to 10.

8. The process according to claim 1, wherein the support has a median pore volume of from 5 to 20 nm.

* * * * *